US008829246B2

(12) United States Patent  
Dubois

(10) Patent No.: US 8,829,246 B2
(45) Date of Patent: Sep. 9, 2014

(54) PROCESS FOR MANUFACTURING ACROLEIN FROM GLYCEROL

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 309 days.

(21) Appl. No.: 12/678,327

(22) PCT Filed: Sep. 11, 2008

(86) PCT No.: PCT/FR2008/051620
§ 371 (c)(1),
(2), (4) Date: Mar. 16, 2010

(87) PCT Pub. No.: WO2009/044081
PCT Pub. Date: Apr. 9, 2009

(65) Prior Publication Data
US 2010/0204502 A1 Aug. 12, 2010

(30) Foreign Application Priority Data

Sep. 20, 2007 (FR) ...................................... 07 57708

(51) Int. Cl.
*C07C 45/52* (2006.01)
*C07C 253/26* (2006.01)
*C07C 51/25* (2006.01)

(52) U.S. Cl.
CPC ............... *C07C 253/26* (2013.01); *C07C 45/52* (2013.01); *C07C 51/252* (2013.01)
USPC ....................................................... 568/486

(58) Field of Classification Search
CPC ...................................................... C07C 45/52
USPC ........................................................ 568/486
See application file for complete search history.

(56) References Cited

U.S. PATENT DOCUMENTS

| 2,558,520 | A |   | 6/1951  | Hoyt et al.     |         |
|-----------|---|---|---------|-----------------|---------|
| 3,094,551 | A |   | 6/1963  | Wood            |         |
| 3,094,552 | A | * | 6/1963  | Wood            | 558/315 |
| 3,142,697 | A |   | 7/1964  | Jennings et al. |         |
| 3,173,962 | A |   | 3/1965  | Carroll et al.  |         |
| 3,314,760 | A |   | 4/1967  | Trapasso        |         |
| 3,716,545 | A |   | 2/1973  | Ripley          |         |
| 3,725,494 | A |   | 4/1973  | Ripley          |         |
| 3,948,959 | A |   | 4/1976  | Cavaterro et al.|         |
| 4,298,755 | A |   | 11/1981 | Daniel et al.   |         |
| 4,331,813 | A |   | 5/1982  | Daniel et al.   |         |
| 4,359,401 | A |   | 11/1982 | Barnett         |         |
| 4,364,856 | A |   | 12/1982 | Teng et al.     |         |
| 4,366,088 | A |   | 12/1982 | Daniel          |         |
| 4,381,411 | A |   | 4/1983  | Pedersen et al. |         |
| 4,473,707 | A | * | 9/1984  | Teng et al.     | 562/599 |
| 5,387,721 | A |   | 2/1995  | Kruse et al.    |         |
| 7,531,699 | B2|   | 5/2009  | Dubois          |         |
| 2008/0183013 | A1 |  | 7/2008 | Dubois et al.  |         |

FOREIGN PATENT DOCUMENTS

| EP | 995491       | 4/2000  |
| EP | 1147807      | 10/2001 |
| FR | 695931       | 12/1930 |
| FR | 2657792      | 5/1992  |
| GB | 616260       | 1/1949  |
| GB | 2090589      | 7/1982  |
| GB | 2195264      | 4/1988  |
| JP | 8-295687     | 11/1996 |
| JP | 10-287610    | 10/1998 |
| JP | 2003-146935  | 5/2003  |
| WO | WO 2008/087315 | 12/2008 |

OTHER PUBLICATIONS

Hanyn et al. "Manufacture of Acrolein" Journal of the Society of Chemical Industry, Japan, 1937, p. 538.*
Chiu et al. "Dehydration of Glycerol to Acetol via Catalytic Reactive Distillation" AIChE Journal, 2006, vol. 52, pp. 3543-3548.*
Malshe et al. "Vapour Phase Oxidation of Acrolein to Acrylic Acid on Mixed Oxides as Catalyst" J. appl. Chem. Biotechnol., 1977, vol. 27, pp. 575-584.*
Hanyn, T. et al., Manufacture of Acrolein, Journal of the Society of Chemical Industry, Japan, vol. 37, No. 9, Jun. 1934, p. 538.
Millet, J-M. et al., Proposal for Active Sites of Iron Phosphates in Isobutyric Oxidative Dehydrogenation Reaction, New Developments in Selective Oxidation, 1990, pp. 833-840, 1990.
Ai, M. et al., Oxidative Dehydrogenation of Isobutraldehyde to Methacolein Over Iron Phosphate Catalyst, Journal of Molecular Catalysis, 89, pp. 371-381, 1994.
Millet, J-M., FePO Catalyst for the Selective Oxidation of Isobutyric Acid Into Methacrylic Acid, Catalysis Review, 40(1), pp. 1-38, 1998.
Beale, A. et al., Following the Structural Changes in Iron Phospate Catalysts by in situ Combined XRD/QuEXAFS Technique, J. Mater. Chem., 12, pp. 3064-3072, 2002.

* cited by examiner

*Primary Examiner* — Joseph Kosack
(74) *Attorney, Agent, or Firm* — Lynn B. Morreale

(57) ABSTRACT

The subject of the present invention is a process for preparing acrolein by dehydration of glycerol in the presence of a catalyst system based on iron phosphorous oxide containing, in addition, one or more elements chosen from alkali metals, alkaline-earth metals, Al, Si, B, Co, Cr, Ni, V, Zn, Zr, Sn, Sb, Ag, Cu, Nb, Mo, Y, Mn, Pt, Rh and the rare earths La, Ce, Sm. The process is preferably carried out in the gas phase in the presence of oxygen starting from aqueous solutions of glycerol. The process according to the invention makes it possible of obtain high acrolein selectivities.

15 Claims, No Drawings

PROCESS FOR MANUFACTURING ACROLEIN FROM GLYCEROL

CROSS-REFERENCE TO RELATED APPLICATIONS

This application is a national stage application under 35 U.S.C.§371 of PCT/FR08/51620, filed Sep. 11, 2008, which claims benefit of FR 07 57708, filed on Sep. 20, 2007 and hereby incorporated by reference.

FIELD OF THE INVENTION

The present invention relates to the production of acrolein and/or acrylic acid from glycerol and, more particularly, one subject of the present invention is a process for preparing acrolein by dehydration of glycerol in the presence of a catalyst system based on iron phosphorus oxide.

BACKGROUND OF THE INVENTION

Fossil resources, such as oil cuts, for the chemical industry will be exhausted in a few decades. Resources of natural and renewable origin such as alternative raw materials are consequently being studied more.

Acrolein, an important synthetic intermediate for the chemical industry is produced industrially by oxidation, in the gas phase, of propylene via the oxygen in the air in the presence of catalyst systems based on mixed oxides. Glycerol, derived from plant oils in the production of biodiesel fuels is one of the routes envisaged as a substitute for propylene, glycerol being able to be subjected to a catalytic dehydration reaction in order to produce acrolein. Such a process makes it possible to thus respond to the concept of green chemistry within a more general context of protecting the environment.

Numerous catalyst systems have already been the subject of studies for the dehydration reaction of glycerol to acrolein.

A process is known from Patent FR 695 931 for preparing acrolein from glycerol according to which acid salts having at least three acid functional groups or mixtures of these salts are used as catalysts. The preparation of these catalysts consists in impregnating, for example with iron phosphate, pumice that has been reduced to pea-sized fragments. According to the teaching of the patent, the yield obtained with this type of catalyst is greater than 80%.

In U.S. Pat. No. 2,558,520, the dehydration reaction is carried out in gas/liquid phase in the presence of diatomaceous earths impregnated with phosphoric acid salts, in suspension in an aromatic solvent. A degree of conversion of glycerol to acrolein of 72.3% is obtained under these conditions.

U.S. Pat. No. 5,387,720 describes a process for producing acrolein by dehydration of glycerol, in liquid phase or in gas phase, at a temperature ranging up to 340° C., over acidic solid catalysts that are defined by their Hammett acidity. The catalysts must have a Hammett acidity below +2 and preferably below −3. These catalysts correspond, for example, to natural or synthetic siliceous materials, such as mordenite, montmorillonite and acidic zeolites; supports, such as oxides or siliceous materials, for example alumina ($Al_2O_3$), titanium oxide ($TiO_2$), covered by monobasic, dibasic or tribasic inorganic acids; oxides or mixed oxides such as gamma-alumina, $ZnO/Al_2O_3$ mixed oxide, or else heteropolyacids. The use of these catalysts would make it possible to solve the problem of formation of secondary products generated with the iron phosphate type catalysts described in the aforementioned document FR 695,931.

According to Application WO 06/087084, the strongly acidic solid catalysts whose Hammett acidity $H_0$ is between −9 and −18 have a strong catalytic activity for the dehydration reaction of glycerol to acrolein and are deactivated less quickly.

However, the catalysts recommended in the prior art for producing acrolein from glycerol generally lead to the formation of by-products such as hydroxypropanone, propanaldehyde, acetaldehyde, acetone, addition products of acrolein to glycerol, polycondensation products of glycerol, cyclic glycerol ethers, but also phenol and polyaromatic compounds which originate from the formation of coke on the catalyst and therefore from its deactivation. The presence of the by-products in acrolein, especially propanaldehyde, poses numerous problems for the separation of acrolein and requires separation and purification steps which lead to high costs for the recovery of the purified acrolein. Furthermore, when acrolein is used for producing acrylic acid, the propanaldehyde present may be oxidized to propionic acid which is difficult to separate from acrylic acid, especially by distillation. These impurities that are present greatly reduce the field of application of the acrolein produced by dehydration of glycerol.

The Inventors have therefore sought to improve the production of acrolein from glycerol, by using more selective catalysts that make it possible to obtain high yields of acrolein and that have an activity over long durations.

Furthermore, numerous applications are known for catalysts mainly composed of iron phosphate. Among these applications, mention may especially be made of:

FR 1 604 884: Oxidation of olefins and diolefins;
U.S. Pat. No. 3,725,494: Process for producing diolefins;
JP 10-287610: Production of methylglyoxyl by oxidation of hydroxyacetone;
JP 2003-146935: Preparation of pyruvic acid by vapour phase oxidation of lactic acid;
U.S. Pat. No. 3,314,760: Production of chloromethane by oxychlorination of methane;
U.S. Pat. No. 3,173,962: Production of olefins and chlorinated hydrocarbons;
GB 616 260: Polymerization and condensation of olefins;
U.S. Pat. No. 3,142,697: Production of nitriles by ammoxidation of an olefin, and more specifically production of acrylonitrile and methacrylonitrile;
JP 8-295687: Production of citraconic anhydride from lactic acid;
FR 2 499 557: Production of alkyl esters by oxydehydrogenation/esterification of mixtures of carboxylic acids and alcohols; and
U.S. Pat. No. 4,381,411: Oxydehydrogenation of saturated aldehydes to unsaturated aldehydes and more specifically for the production of acrolein and methacrolein.

The use of catalyst systems based on iron phosphate for the oxydehydrogenation of saturated carboxylic acids to unsaturated carboxylic acids, in particular the conversion of isobutyric acid to methacrylic acid has been widely described:

Mention may be made of Patent Application FR 2,514,756 which describes the oxydehydrogenation reaction of isobutyric acid in the presence of a calcined iron phosphate containing an extrinsic metal such as silver, lanthanum, cobalt or tellurium, as a modifier compound or dopant.

In Patent Application FR 2 497 795, the same reaction is carried out in the presence of an iron phosphate modified by the presence of a metal chosen from boron, aluminium, gallium and indium. It has been found that the iron phosphate catalyst modified by aluminium is active for long durations for the oxydehydrogenation reaction of isobutyric acid.

Patent Application FR 2 245 604 describes a process for preparing α,β-unsaturated acids by dehydrogenation, which is oxidizing due to the action of oxygen or of a gas containing oxygen, of saturated aliphatic carboxylic acids in the presence of a catalyst containing, in combination with the oxygen, iron, phosphorus and optionally one or more elements belonging to the list formed by lithium, sodium, potassium, rubidium, caesium, magnesium, calcium, strontium, barium, tin and antimony. This catalyst composition may be used without any support or in combination with a support.

Also known from Patents U.S. Pat. Nos. 4,364,856 and 4,473,707 is a catalyst based on iron phosphorus oxide, which is in a coated form on a support. Such a catalyst is denoted hereinafter by the expression "coated catalyst". Its preparation process consists in partially wetting a support, such as silica, with a colloidal suspension or solution of $SiO_2$ in water; putting the partially wetted support in contact with a powder of the catalyst; and stirring the mixture thus produced to form the coated catalyst, which is then dried, and calcined. The actual catalyst is represented by the empirical formula $A_aFe_bP_cD_dO_x$, where:

A is chosen from Al, B, Be, Cd, Co, Cr, Ga, Ge, In, Ni, Te, Th, Ti, Tl, U, V, Zn, Zr, rare earths and mixtures thereof;
D is chosen from Ag, Cu, Mn and mixtures thereof; and
$a=0$-$1.0$; $b=0.75$-$1.5$; $c=1.0$-$2.0$; $d=0$-$2.0$; a+d is greater than 0; and x is the number of oxygen atoms necessary to satisfy the valency requirements of the remaining elements.

Also known, from Patent CA-A-1 186 673, is a two-component catalyst system comprising, as a physical mixture, an iron/phosphate type catalyst and an inert (silica) support doped with phosphate, said support being prepared by formation of an aqueous slurry of an inert support and of phosphoric acid, removal of the solvent by evaporation to form a dried mass and calcination of the dried mass.

Described in Patent Application FR 2 657 792 is a catalyst of general formula $FeP_xMe_yO_z$, in which:

Me represents at least one of the following elements: Li, Na, K, Rb, Cs, Mg, Ca, Sr and Ba;
x has a value of 0.2 to 3.0;
y has a value of 0.1 to 2.0; and
z is the amount of oxygen bonded to the other elements and that corresponds to their oxidation state, this catalyst being combined with a support, characterized by the fact that said support is a fully impregnable macroporous support having a specific surface area less than or equal to 1 $m^2/g$, a pore volume between 0.2 and 1 $cm^3/g$ and an average pore diameter greater than or equal to 1 micron, and that the active material is deposited on the surface of all the pores of said support, said catalyst being in the form of support grains impregnated with active material, which have a size between 0.5 and 10 mm.

It is known from document FR 2 498 475 to use a catalyst support to which a phosphate has been added by physical mixing with the catalyst that contains a phosphate, thus making it possible to partly solve the problem of extraction of phosphate during the use of the catalyst in the preparation of methacrylic acid from isobutyric acid and oxygen.

DETAILED DESCRIPTION OF THE INVENTION

It has now been found that the use of catalyst systems based on iron phosphorus oxide and comprising a modifier compound or dopant, for the dehydration reaction of glycerol to acrolein makes it possible not only to obtain high acrolein selectivities, but also to solve the deactivation problem encountered with the catalysts conventionally used for this reaction. Although it seems that the oxidation/reduction couple involved in the base reaction can be attributed to the iron phosphate, the species with catalytic activity has or have not been identified, but it appears that the presence of an extrinsic metallic compound in the preparation of the catalyst system facilitates the formation of the species with catalytic activity. This catalyst system has the advantage of being active with respect to the secondary product propanaldehyde optionally formed during the dehydration of glycerol in order to convert it to acrolein and thus to result in excellent selectivities and yields.

The subject of the present invention is therefore a process for manufacturing acrolein from glycerol, characterized in that the reaction for dehydration of glycerol is carried out in the presence of a catalyst system comprising oxygen, iron, phosphorus, and one or more elements chosen from alkali metals, alkaline-earth metals, Al, Si, B, Co, Cr, Ni, V, Zn, Zr, Sn, Sb, Ag, Cu, Nb, Mo, Y, Mn, Pt, Rh and the rare earths La, Ce, Sm.

Preferably, the catalyst system comprises a catalyst corresponding to the general formula $FeP_xM'_yM''_wO_z$ in which:

M' represents at least one of the following elements: alkali metal, alkaline-earth metal, Al, B, Co, Ni, Sn, Sb, Mn, Ag, alone or as a mixture, M" represents at least one of the following elements: Pt or Rh, alone or as a mixture;
x ranging from 0.2 to 3.0, limits included, preferably ranging from 0.9 to 2.0;
y ranging from 0.01 to 2.0, limits included;
w ranging from 0.0 to 0.1, limits included; and
z is the amount of oxygen bound to the other elements and corresponding to their oxidation state.

The elements Cs, Al, B and Ag are preferred as the metal M'.

The catalyst system in the process according to the invention may be a bulk catalyst and is in this case used without any support resulting, as is, in an excellent catalytic activity.

As starting compounds for obtaining the catalytic composition of the process of the present invention, it is possible to use, for example, for the iron compounds: nitrates, chlorides, sulphates, carbonates, organic monocarboxylic or polycarboxylic acid salts, chelates, etc. As phosphorus-based compounds, it is possible to use alkali metal phosphates, ammonium phosphates, and phosphoric and phosphorous acids, etc. As alkali or alkaline-earth metal compounds, it is possible to use, for example, the following compounds: nitrates, oxides, hydroxides, chlorides, sulphates, carbonates, bicarbonates, nitrites, phosphates, silicates, and also the salts of oxyacids or of organic monocarboxylic or polycarboxylic acids such as formates, oxalates, citrates, tartrates, etc. As compounds of other elements, it is possible to use, for example, oxides, halides, sulphates, organic monocarboxylic or polycarboxylic acid salts, etc.

The catalyst may be prepared according to any method that is already known, all the preparation methods comprising a final activation step of the catalytic composition, which generally consists of a calcination at a temperature between 350 and 1000° C.

The most common methods comprise the preparation of an integral composition before the calcination. This may easily be carried out by using the so-called slurry method or the precipitation method. In the latter method, an aqueous solution of salts of the metals in question and of phosphoric acid is prepared first and is then neutralized with a suitable base in order to precipitate the mixed metal phosphates. It is advantageous to carefully wash the precipitate in order to separate all traces of water-soluble substances and then to dry it before the calcination. Alternatively, it is possible to add ammonium phosphate to the solution of the metal salts in order to directly precipitate the metal phosphates. It is possible to use any water-soluble iron or metal salts. However, due to the solubility properties of nitrates, these salts are preferred.

The so-called slurry method is also well suited for preparing the catalysts used in the process of the invention. According to this procedure, the aqueous solution of the salts of iron and of the metal in question together with phosphoric acid is obtained. The solution is heated continuously until the mass can no longer be stirred. Next, the residue is broken up and it is heated again to a fairly high temperature of the order of around 120° C. until completely dry. Next, the product is screened and calcined.

According to one or the other of these techniques, it is possible to prepare a catalyst on a support. It is possible to use, as the support, any material such as silica, alumina, titanium oxide, silicon carbide, silica/alumina mixture, silicates, borates or carbonates on condition that these products are stable under the reaction conditions to which the catalyst will be subjected. The support is added before removing the moisture content. The support may also be impregnated in a solution of the metal phosphate and dried. The impregnation and drying steps should be repeated until the desired number of layers of dry metal phosphate are obtained. Similarly, in the alternative method described, it is possible to carry out the precipitation of the metal phosphates in the presence of suspended particles of the designated support. It is possible to then use a spray-drying technique in which the slurry is introduced into the drier by spraying and the solid product is then compressed or extruded and then calcined.

Other methods such as those indicated below may also be used to prepare the catalysts that can be used in the invention:

Salts of alkali or alkaline-earth metal compounds are dissolved in concentrated phosphoric acid, then hydrated iron nitrate is added. The solution is then evaporated, the recovered solid is dried, then milled and screened. Next 1 wt % of carbon black is added before pelleting the solid in the form of hollow cylindrical pellets, for example having a height of 3.5 mm, an inner diameter of 1.5 mm and an outer diameter of 5 mm. The solid is finally calcined at 460° C.

The desired amount of an iron-containing compound is dissolved in a solvent such as water. The appropriate amount of phosphorus in the form of an acid or of a TO solution of dissolved salt is incorporated therein. Colloidal silica may also be added up to 15 wt % relative to the resulting mixture in order to give the catalyst the desired physical strength. The pH of the solution is then adjusted to 7 by addition of a base, which results in the formation of a precipitate of crude iron/phosphate catalyst which is dried after washing, after combination with alkali or alkaline-earth metal salts, or another envisaged dopant element. As a variant, it is possible to add the alkali or alkaline-earth metal salts to the solution of iron and phosphorus salt before neutralization. After drying, the catalyst is milled to the desired fineness, then calcined.

In one particular embodiment of the invention, the catalyst may be combined with a fully impregnable macroporous support, the active material being deposited on the surface of all the pores of the support. The catalyst support may also have a phosphate added to it as a physical mixture with the active material containing the iron phosphate.

The molar ratio of the phosphorus to the inert support material may vary over a wide range. Generally, the P/support ratio may vary from 20/1 to 1/30. This ratio naturally varies depending on the type of the support material, taking into account that the latter should give the catalyst mechanical strength and increase its specific surface area.

It will be possible to refer more specifically to the documents of the prior art cited previously for the oxydehydrogenation reaction of saturated carboxylic acids in order to use the most suitable method for preparing the doped catalysts based on iron phosphate that can be used for the process of the invention.

It is also possible to prepare the catalysts for the process according to the invention by variations on the general methods described in the following documents:

J M Millet, J C Védrine and G. Hecquet, in "New Developments in Selective Oxidation", (1990), page 833, Elsevier Science Publishers, G. Centi and F Trifiro Eds;

Ai et al., J. Mol. Catal. 89 (1984) 371-381;

J M Millet, Catalysis Review 40:1, page 1-38; and

A M Beale et al., J. Mat. Chem. 12 (2002) 3064-3072.

The process according to the invention may be carried out in the gas phase or in the liquid phase, preferably in the gas phase. When the dehydration reaction is carried out in the gas phase, various process technologies may be used, namely fixed-bed process, fluidized-bed process or circulating fluidized-bed process. Plate heat exchanger reactors, such as those described, for example, in the documents EP 995 491 or EP 1 147 807, may also be used.

The dehydration of glycerol may also be carried out in the liquid phase in a conventional reactor for a liquid phase reaction, but also in a catalytic distillation type reactor. Given the large difference between the boiling points of glycerol (280° C.) and acrolein (53° C.), it is also possible to envisage a liquid-phase process at a relatively low temperature which allows a continuous distillation of the acrolein produced. The reaction is permanently displaced thus limiting the consecutive reactions on the acrolein in a continuous reactor at equilibrium displacement.

The experimental conditions of the gas-phase reaction are preferably a temperature between 180° C. and 500° C., preferably between 250 and 400° C. and a pressure between 1 and 5 bar. In the liquid phase, the reaction is preferably carried out at a temperature between 150° C. and 350° C. and a pressure which may range from 3 to 70 bar.

In the process of the invention, an aqueous solution of glycerol is generally used that has a concentration ranging from 20% to 99%, preferably between 30% and 80%, by weight in the reactor.

The solution of glycerol may be used in liquid form or in gaseous form, preferably in the gas-phase form.

One preferred embodiment of the invention will now be described. The process for preparing acrolein from glycerol consists in sending a mixture containing at least glycerol, water, oxygen or an oxygen-containing gas, and where appropriate an inert gas and/or recycle gases, in the gas phase, to a bed of a catalyst system such as defined previously, kept at a reaction temperature between 180 and 500° C.

The charge sent into the reactor may be preheated to a preheating temperature of the order of around 180° C. to 350° C.

The process is carried out at a pressure around atmospheric pressure and more precisely, preferably, at a slightly higher pressure.

The amount of oxygen is chosen so as to be outside the explosive limit at any point of the installation. The molar ratio of the molecular oxygen to the glycerol is generally around 0.1 to 1.5, preferably from 0.5 to 1.0.

Another parameter lies in the concentration of glycerol in the charge. Expressed in mole percent, the concentration of glycerol varies widely from 0.1 to 20. As is common in reactions of this type, the yield of the desired product is an inverse function of the concentration. From the point of view of obtaining a reasonable flow rate combined with an acceptable yield, the concentration of the glycerol in the charge is around 3 to 16 mol %. The concentration is controlled by the amount of water and of inert gas present in the feed stream. The preferred gaseous diluent is nitrogen although other gases such as carbon dioxide, helium, argon, etc. are also suitable. Of course, when the desired concentration of glycerol permits it, air represents a suitable diluted oxidant.

The contact time, expressed in seconds, is the ratio of the volume of the catalyst bed to the volume of gaseous reactants conveyed per second. The average temperature and pressure conditions in a bed may vary depending on the nature of the catalyst, the nature of the catalyst bed and the size of the catalyst. Generally, the contact time is from 0.1 to 20 seconds and preferably from 0.3 to 15 seconds.

The catalysts used in the process of the present invention make it possible to attain high yields of acrolein with extremely high conversion rates which may, in certain cases, reach up to 100% of glycerol. These results are due to the fact that these catalysts have the advantage of promoting a dehydration process that progresses evenly and is easily controllable with regard to the reaction temperatures and contact times. The reactants may be introduced onto the catalyst, whether the former are already completely or only partially premixed, or may be introduced individually.

The supply of various reactants, applied to a fixed-bed or to a fluidized-bed reactor may be carried out individually or already in the form of premixes. It is also possible to introduce part of the air or optionally all of the glycerol or only part of this glycerol into the bottom of the reactor and to successively supply the remaining parts of the reactant to one or more intermediate points of the catalyst bed. When the reaction is carried out according to fixed catalyst bed techniques, such beds may be obtained according to known methods by placing the catalyst in the tubes of a multitube reactor and by removal of their heat of reaction using suitable fluids flowing on the outside of the tubes, these fluids possibly, for example, and more generally consisting of mixtures of molten salts. It is also possible to operate in a reactor having several adiabatic reaction stages separated by zones for cooling the reaction mixture.

According to one particular embodiment of the invention, it is possible to place, upstream of the doped catalyst system based on iron phosphate, a first active catalyst bed, or a first reactor enabling the dehydration reaction of glycerol to acrolein to be carried out. The gaseous reaction mixture is thus sent to a first catalyst in contact with which the dehydration reaction of glycerol is at least partially carried out generally resulting in secondary compounds such as propanaldehyde. The reaction mixture thus obtained is then in contact with the catalyst system on which the dehydration reaction of unreacted glycerol may continue at the same time as the conversion of propanaldehyde to acrolein. The first catalyst bed may operate at a lower temperature than the second catalyst bed, thus optimizing the energy balance of the process. The acrolein obtained according to this embodiment contains a minimized amount of propanaldehyde, which widens its field of application. This configuration of reactors is possible according to various technologies, for example as an adiabatic fixed bed, but also as a multitubular fixed bed, or else, for example, as a compartmentalized fluidized bed. It is also possible in the case where the first reactor operates in the liquid phase and the second containing the catalyst based on iron phosphate operates in the gas phase.

Over a long period of use, the catalyst system may tend to be less effective both in relation to the degree of conversion and the selectivity. The catalyst will then be subjected to a regeneration step, for example according to the method described in document FR 2 498 476 which consists in subjecting the catalyst based on iron phosphate to a strongly oxidizing atmosphere at around 350° C. for at least a period of two hours, then in subjecting it to a reducing atmosphere at around the same temperature.

Other regeneration methods may be used, especially that described in document EP 263 005 consisting in regenerating the catalyst by addition of a phosphorus-containing compound, or that described in document U.S. Pat. No. 3,716,545 consisting in adding phosphorus during the process in order to increase or maintain the activity of the catalyst.

The invention also relates to the use of a catalyst system comprising oxygen, iron, phosphorus, and one or more elements chosen from alkali metals, alkaline-earth metals, Al, Si, B, Co, Cr, Ni, V, Zn, Zr, Sn, Sb, Ag, Cu, Nb, Mo, Y, Mn, Pt, Rh and the rare earths La, Ce, Sm for carrying out the dehydration reaction of glycerol to acrolein.

It would not constitute a departure from the scope of the present invention if the method were carried out in the presence of a propylene-containing gas, as described in the Application WO 07/090990.

The invention also relates to a process for preparing acrylic acid from glycerol comprising a first step of preparing acrolein according to the process described previously and a step of oxidizing acrolein to acrylic acid.

The invention also relates to a process for preparing acrylic acid from glycerol comprising a first step of preparing acrolein according to the process described previously and a second step of oxidizing acrolein to acrylic acid in which an intermediate step of partial condensation of the water and of the heavy by-products from the first step is carried out, as described in Application WO 08/087315.

The invention also relates to a process for preparing acrylonitrile from glycerol comprising a first step of preparing acrolein according to the process described previously, and a step of ammoxidation of the acrolein to acrylonitrile.

The catalyst systems that can be used in the process of the present invention may also be used to promote an oxydehydration reaction of glycerol to acrylic acid; a person skilled in the art will determine, in this case, the operating conditions to use.

The following examples illustrate the present invention without however limiting the scope thereof.

EXAMPLES

In the examples which follow, the expression "acrolein selectivity" (in %) is understood to mean the ratio: number of moles of acrolein formed/number of moles of glycerol having reacted×100, the acrolein yield (in %) is the ratio: number of moles of acrolein formed/number of moles of glycerol introduced×100, the reaction gases being analyzed by gas chromatography.

Example 1 (Comparative)

By using the $Fe_1P_2$ catalyst prepared according to Example 1 from document FR 2 245 604 in the form of a fixed bed in a reactor fed by a gaseous mixture composed of glycerol, air, water vapour and nitrogen in the molar proportions 1/3.13/ 15/55 at a temperature of 320° C. and for a contact time of 2 s, it was possible to obtain an acrolein selectivity of 65%.

Example 2

By using the catalyst prepared according to Example 8 of document FR 2 245 604, corresponding to the empirical formula $Fe_1P_{1.84}Cs_{0.66}$, in the form of a fixed bed in a reactor fed by a gaseous mixture composed of glycerol, air, water vapour and nitrogen in the molar proportions 1/3.1125/55 at a temperature of 380° C. and for a contact time of 0.5 s, it was possible to obtain an acrolein selectivity of 75%.

Example 3

By using the catalyst prepared according to Example 15 of document FR 2 245 604, corresponding to the empirical formula $Fe_1P_{1.4}Sr_{0.25}$, in the form of a fixed bed in a reactor fed by a gaseous mixture composed of glycerol, air, water vapour and nitrogen in the molar proportions 1/3.6/25/55 at a temperature of 380° C. and for a contact time of 1 s, it was possible to obtain an acrolein selectivity of 70%.

Example 4

A tubular reactor containing a fixed bed of catalyst corresponding to the formula $Fe_{1.0}Cs_{0.1}P_{1.26}O_x/SiO_2$ at 320° C. was fed at a feed rate of 8.5 ml/h with glycerol, at 30.0 ml/h with water and at 120.0 ml/min with air. it was possible to obtain, under these conditions, a degree of conversion of 95% of glycerol and a yield 76% of acrolein.

Example 5

Use is made of a catalyst prepared according to Example 16 of document FR 2 245 604, corresponding to the empirical formula $Fe_1P_{1.84}K_{0.66}$. The dehydration reaction is carried out in a reactor containing this catalyst in the form of a fluidized bed and fed by a gaseous mixture composed of glycerol, air and water vapour in the molar proportions 1/2.5/ 44 at a temperature of 330° C., and for a contact time of 1.3 s. By gas chromatographic analysis of the reaction gases, a degree of conversion of the glycerol of 87% and an acrolein selectivity of 71% were obtained.

Example 6

A catalyst corresponding to the empirical formula $Fe_1P_{1.44}Ag_{0.18}O_x$ is prepared in the following manner: 103.2 g of iron nitrate nonahydrate is dissolved with 7.5 g of silver nitrate in 200 ml of distilled water. Added to this solution are 35.8 g of concentrated phosphoric acid with 30 cm³ of silica gel containing 20% $SiO_2$. The solution is stirred at 85° C. until most of the water has evaporated. The paste obtained is dried at 120° C. until the water appears to have completely evaporated, then the heating is continued at 150° C. overnight. The dry product is then calcined at 450° C. for 16 h, then at 520° C. for 2 h.

15 cm³ of this catalyst is introduced into a reactor in order to form a fixed bed kept at a temperature of 385° C. The reactor is fed with a flow rate of 41 l/h by a gaseous mixture composed of glycerol, oxygen, water vapour and nitrogen in the molar proportions 1/1/25/20. A degree of conversion of the glycerol of 86% and an acrolein selectivity of 68% are obtained.

Example 7

404.4 g of iron nitrate nonahydrate is dissolved with 127.2 g of 85% (weight of $H_3PO_4$) phosphoric acid in 400 ml of distilled water. Added to the solution obtained are 100 ml of silica sol containing 40% silicon dioxide (Ludox AS40). The solution obtained is stirred at 85° C. until most of the water has evaporated. The paste obtained is dried again at 120° C. until it can be fragmented, then the drying is continued for 12 h. The dried mixture is calcined at 460° C. for 6 h.

The solid obtained is then impregnated with a solution of chloroplatinic acid. An incipient wetness impregnation is carried out.

The empirical formula of the calcined composition is the following: $FeP_{1.3}Si_{0.67}Pt_{0.02}O_x$.

The catalyst, in the form of grains of 65 to 150 microns in a fixed bed is fed by a gaseous mixture of glycerol, air, water vapour and nitrogen in the molar proportions 3/20/60/15 at a temperature of 300° C. and for a contact time of 2 seconds. An acrolein yield of 53% is obtained.

The invention claimed is:

1. Process for manufacturing acrolein from glycerol, comprising dehydrating glycerol in the presence of a catalyst system which is a hulk catalyst used without any support and activated by a final calcination step, said hulk catalyst consisting of oxygen, iron, phosphorus, and one or more elements selected from the group consisting of alkali metals, alkaline-earth metals, Al, Si, B, Co, Cr, Ni, V, Zn, Zr, Sn, Sb, Ag, Cu, Nb, Mo, Y, Mn, Pt, Rh and rare earths La, Ce, Sm, wherein one or more elements is provided as hulk modifier compound or dopant to the catalyst system.

2. Process according to claim 1, characterized in that a first active catalyst bed or a first reactor enabling the dehydration reaction of glycerol to acrolein to be carried out is placed upstream of the catalyst system comprising the aforementioned elements.

3. Process according to claim 1, characterized in that a mixture containing at least glycerol, water, oxygen or an oxygen-containing gas, and optionally an inert gas and/or recycle gases, in the gas phase, is passed over the catalyst system kept at a reaction temperature between 180 and 500° C.

4. Process of claims 1 further comprising a step of oxidizing acrolein to acrylic acid.

5. Process according to claim 4, further comprising an intermediate step of partial condensation of water and of heavy by-products prior to said step of oxidizing acirolein to acrylic acid.

6. Process of claim 1 further comprising a step of ammoxidation of acrolein to acrylonitrile.

7. Process for manufacturing acrolein from glycerol, comprising dehydrating glycerol in the presence of a catalyst system comprising a catalyst corresponding to the general formula $FeP_xM'_yM''_wO_z$ in which:

M' is selected from the group consisting of: alkali metal, alkaline-earth metal, Al, B, Co, Ni, Sn, Sb, Mn, Ag, and mixtures thereof, M" is selected from the group consisting of Pt or Rh, and mixtures thereof;

x is from 0.2 to 3.0, limits included;

y is from 0.01 to 2.0, limits included;

w is from 0.0 to 0.1, limits included; and z is the amount of oxygen bound to the other elements and corresponding to their oxidation state.

8. The process according to claim 7, wherein M' selected from the group consisting of Cs, Al, B and Ag.

9. The process according to claim 7, wherein x is from 0.9 to 2.0.

10. The process according to claim 7, wherein the catalyst system further comprises a support selected from the group consisting of silica, alumina, titanium oxide, silicon carbide, silica/alumina mixture, silicates, borates and carbonate.

11. The process according to claim 7, wherein a first active catalyst bed or a first reactor enabling the dehydration reaction of glycerol to acrolein to be carried out is placed upstream of the catalyst system comprising the aforementioned elements.

12. The process according to claim 7, wherein a mixture containing at least glycerol, water, oxygen or an oxygen-containing gas, and optionally an inert gas and/or recycle gases, in the gas phase, is passed over the catalyst system kept at a reaction temperature between 180 and 500° C.

13. The process of claim 7 further comprising a step of oxidizing acrolein to acrylic acid.

14. The process according to claim 13, further comprising an intermediate step of partial condensation of water and heavy by-products prior to said step of oxidizing acrolein to acrylic acid.

15. The process of claim 7 further comprising a step of ammoxidation of acrolein to acrylonitrile.

* * * * *